United States Patent [19]

Houser

[11] 4,448,311

[45] May 15, 1984

[54] SAMPLE CELL

[75] Inventor: Edwin A. Houser, Fullerton, Calif.

[73] Assignee: Tech Ref, Inc., Fullerton, Calif.

[21] Appl. No.: 460,310

[22] Filed: Jan. 24, 1983

[51] Int. Cl.³ ............................................. G01N 21/00
[52] U.S. Cl. ..................................... 206/527; 220/319;
 220/269; 206/628; 356/246; 378/204; 378/208
[58] Field of Search ...................... 206/527, 525, 45.32,
 206/45.34, 497, 628; 220/319, 269; 38/102.2;
 378/204; 250/456; 356/246

[56] References Cited

U.S. PATENT DOCUMENTS

| | | | |
|---|---|---|---|
| 627,821 | 6/1899 | Gurnee | 38/102.2 |
| 3,195,718 | 7/1965 | Sobel | 206/45.32 |
| 3,335,848 | 8/1967 | Frankenberg et al. | 206/45.34 |
| 3,523,863 | 8/1970 | Juhos | 206/497 |
| 4,346,299 | 8/1982 | Mitteldorf et al. | 220/319 |

*Primary Examiner*—William T. Dixson, Jr.
*Attorney, Agent, or Firm*—Fulwider, Patton, Rieber, Lee & Utecht

[57] ABSTRACT

A sample cell useful in analytical devices employing X-ray fluorescence as the detection method. The sample cell includes a cup which telescopically receives a ring. A radiation permeable membrane is sandwiched between the outside of the cup and the inside of the ring so as to be tightly stretched across the cup. The cup and ring are both molded from virgin polyethylene mixed with a silicone oil.

8 Claims, 4 Drawing Figures

SAMPLE CELL

BACKGROUND OF THE INVENTION

1. Field of the Invention

The present invention relates to an improved sample cell useful with fluorescent X-ray analytical devices employing X-ray flouorescence as the method of detection.

2. Description of the Prior Art

A typical sample cell for use with fluorescent X-ray analytical devices is disclosed in U.S. Pat. No. 4,037,190 granted July 19, 1977. The sample cell shown in such patent includes telescopically interfitting parts molded from synthetic plastics such as nylon, polypropylene, or polyester. When the parts of such sample cell are fitted together they support a radiation permeable membrane so as to define a liquid sample-receiving surface. The liquid sample is analyzed and thereafter the plastic parts of the sample cell are discarded.

A more recent sample cell of this nature utilizes a cup and a ring which is telescopically slideably received by the exterior of the cup, with a radiation permeable membrane being sandwiched therebetween so as to be tightly stretched across the cup to thereby present a uniform flat surface to the received radiation when inverted. The cup and ring members are formed of polyethylene. This type of sample cell utilizes fewer parts than the sample cell disclosed in U.S. Pat. No. 4,037,109. It has been found, however, that in order to tightly and uniformly stretch the membrane across the top of the cup, the cup and the ring must be tightly interfitted. In view of the tight-fitting relationship between the cup and the ring, the membrane tends to bind over the lip of the cup and often either tears or puckers. To overcome this problem, it has been proposed to apply a lubricating film to the mating surfaces of the cup and the ring. A considerable amount of time however, is required to apply lubricant to the cup since it is essential that the lubricant not contact the interior of the cup so as to contaminate the liquid samples received therein. This type of sample cup also utilized a parting line on the cup adjacent to the lip of the cup. The presence of such parting line at that point was found to contribute to breakage of the membrane on the sharp edge defined by the parting line.

SUMMARY OF THE INVENTION

The present invention eliminates the disadvantages of prior art sample cups by forming the cup and the ring of a molded synthetic plastic mixed with a lubricant so as to completely eliminate the danger of contamination of the liquid sample to be analyzed while providing the required flat, wrinkle-free membrane surface. The improved sample cup of the present invention also eliminates the use of a parting line adjacent the lip of the cup and instead positions such parting line on the inner wall of the cup below the membrane-engaging lip of the cup.

DETAILED DESCRIPTION OF A PREFERRED EMBODIMENT

Figure 1:
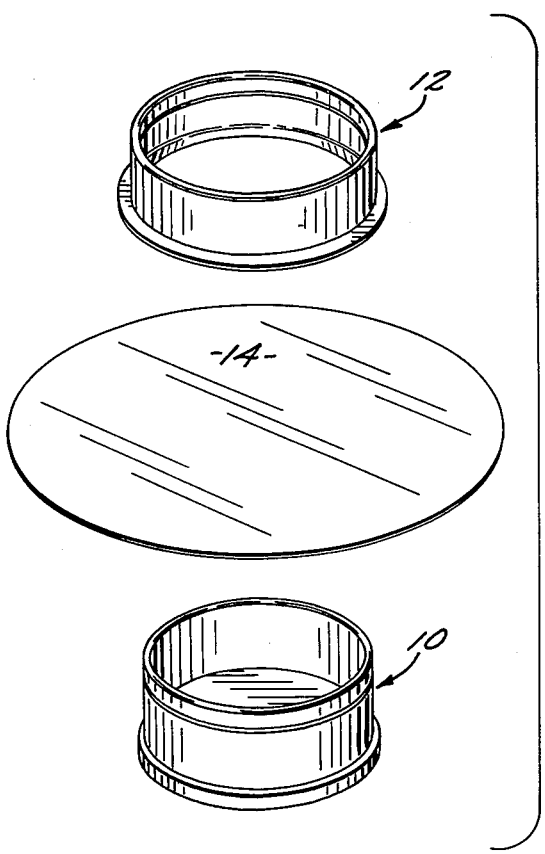
FIG. 1 is a vertically exploded perspective view of a preferred form of an improved sample cell embodying the present invention.
Figure 2:
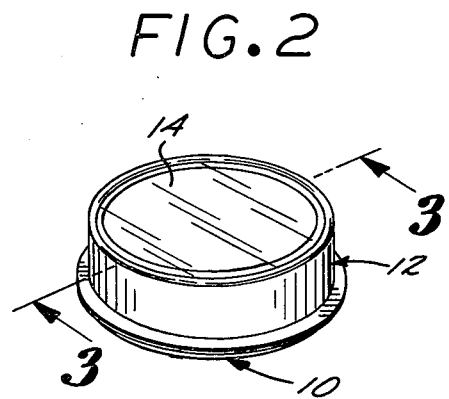
FIG. 2 is a perspective view showing the parts of said improved sample cup assembled.

Referring to the drawings, a preferred form of improved sample cell embodying the present invention includes a cup member, generally designated 10, and a ring member, generally designated 12, with the ring member being telescopically slideably received by the exterior of the cup member. A radiation permeable membrane 14 is sandwiched between the cup and ring members when the latter are telescopically engaged so as to be tightly stretched across the top of the cup, as indicated in FIG. 2. The cavity 16 formed between the underside of membrane 14 receives a liquid sample 18 for fluorescent analysis.

More particularly, cup member 10 is of intregal molded construction and includes upstanding sidewalls 20 the lower ends of which are bridged by a horizontal wall 22. An annular base 24 of larger diameter than the sidewalls depends from base wall 16. Ring member 12, includes an annular wall 26, the bottom of which is formed with a flange 28. Ring member 12, like cup member 10, is of intregal molded construction. The lower interior portion of ring member 12 is formed with a flared surface 29 to facilitate placement of membrane 14.

Figure 4:
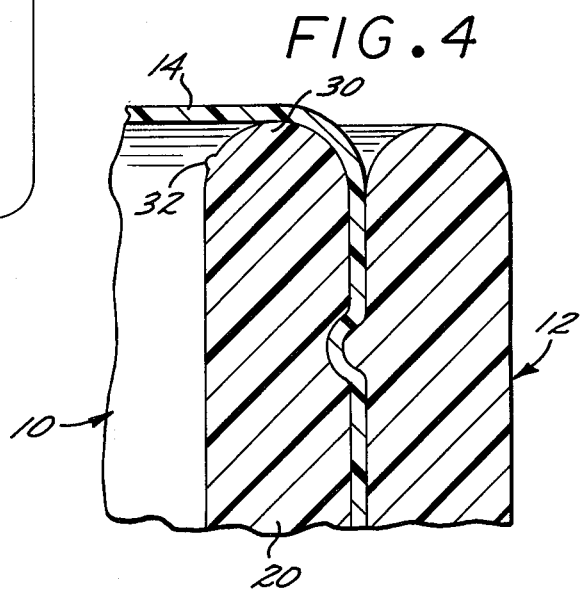
FIG. 4 is a further enlarged view of the encircled area designated 4 in FIG. 3.
Figure 3:
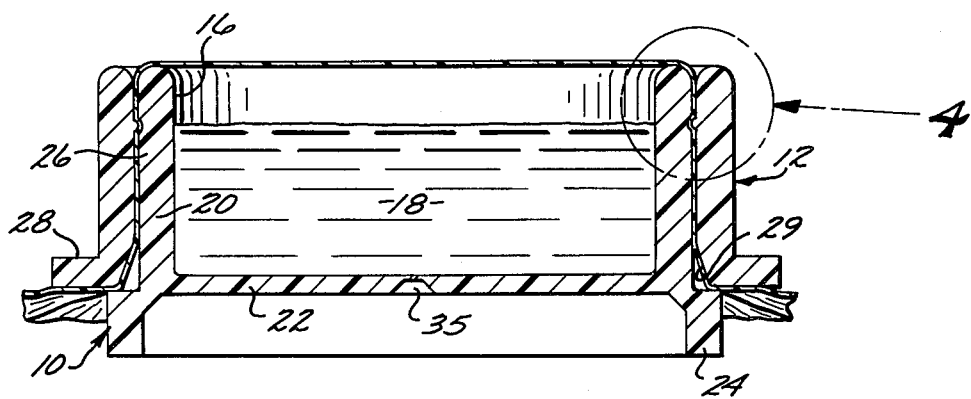
FIG. 3 is a vertical sectional view taken in enlarged scale along line 3—3 of FIG. 2.

Referring now to FIG. 4, the extremity of the lip portion 30 of cup member C includes an interior mold parting line 32 which is spaced away and therefore out of contact with membrane 14. With continued reference with FIG. 4, the exterior surface of cup sidewalls 20 is formed with a recess 34 which releasably engages a complimentary rib 36 formed on the interior surface of the ring member when the cup and ring member are interfitted. Cavity 16 may be readily vented by puncturing base wall 22 at dimple 35.

To assemble the parts of the improved sample cell described hereinabove, membrane 14 is disposed across the lip 30 of cup member 10. Thereafter, ring member 12 is lowered over the outside of the cup member until its rib 36 is circumferentially aligned with the recess 34 of the cup member. This interfitting of the cup and ring members serves to tightly stretch the membrane 14 across the lip 30 of the cup member, with the space between the interior of the membrane and the cavity 16 of the cup member forming a chamber for the liquid sample 18 to be analyzed. It is important to note that the mold parting line 32 of the cup member does not come into contact with the membrane and accordingly the danger of damaging contact between the membrane and the parting line is eliminated. The membrane 14 is accordingly provided with a smooth, flat surface where it engages the lip 30 when the assembled cup and ring members are inverted in an analyzer (not shown), the X-rays from such analyzer coming from below the membrane.

Both the aforedescribed cup and ring members are molded from a synthetic plastic mixed with a lubricant so as to reduce the coefficient of friction between these members and the membrane to the point that the membrane will neither break nor pucker or wrinkle when stretched over the lip of the cup as the ring is interfitted with the cup. It has been found that where the ring and cup members are molded of a virgin polyethylene, a lubricant such as a silicone oil having viscosity of about 60,000 cst in a proportion of approximately 2-5% by weight of silicone oil to virgin polyethylene provides excellent results. It has also been found that with this arrangement the silicone tends to migrate to the surface of the cup and ring members to provide the desired coefficient of friction, yet the silicone will not contaminate the liquid sample 18.

It must be kept in mind that the sample cell of the present invention described hereinbefore is simply illustrative and should be taken by way of an example, and does not in any manner limit the scope and spirit of the invention as claimed. Alterations and modifications may be made by one with ordinary skill in the art, once provided with the teachings of the present invention, which modifications and alterations do not depart from the spirit and scope of the claimed invention. By way of example, a synthetic plastic other than polyethylene and a lubricant other than silicone may provide satisfactory results.

I claim:

1. A sample cell for use with a radiation permeable membrane, in analyzing a liquid sample, said sample cell comprising:

A cup member having upstanding side walls and a bottom wall;

a ring member telescopically slideably received by the exterior of the side walls of said cup with the intermediate portion of said membrane sandwiched therebetween so as to be tightly stretched across the top of said side walls;

complementary releasable rib and recess means interposed between said members; and said cup and ring being molded from a synthetic plastic mixed with a lubricant.

2. A sample cell as set forth in claim 1, wherein the synthetic plastic is virgin polyethylene and the lubricant is silicone oil mixed in a proportion by weight of approximately 2–5%.

3. A sample cell as set forth in claim 1, wherein a parting line is formed on the inner wall of said ring below the top of the side walls of said cup, said parting line being out of contact with said membrane.

4. A sample cell as set forth in claim 1, wherein the lower interior portion of said ring member is formed with a flared surface to facilitate placement of the membrane.

5. A sample cell as set forth in claim 2, wherein the silicone oil has a viscosity of about 60,000 cst.

6. A sample cell as set forth in claim 2, wherein a parting line is formed on the inner wall of said ring below the top of the side walls of said cup, said parting line being out of contact with said membrane.

7. A sample cell as set forth in claim 4, wherein a parting line is formed on the inner wall of said ring below the top of the side walls of said cup, said parting line being out of contact with said membrane.

8. A sample cell as set forth in claim 3, wherein the lower interior portion of said ring member is formed with a flared surface to facilitate placement of the membrane.

* * * * *